(12) United States Patent
Takeuchi et al.

(10) Patent No.: US 9,090,912 B1
(45) Date of Patent: Jul. 28, 2015

(54) NUCLEIC ACID COMPLEX AND NUCLEIC ACID-DELIVERING COMPOSITION

(75) Inventors: Hirofumi Takeuchi, Gifu (JP); Yuichi Tozuka, Gifu (JP); Mitsutaka Murata, Gifu (JP); Hidekazu Toyobuku, Osaka (JP)

(73) Assignees: Hirofumi Takeuchi, Gifu (JP); OTSUKA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 13/254,770

(22) PCT Filed: Mar. 4, 2010

(86) PCT No.: PCT/JP2010/053581
§ 371 (c)(1),
(2), (4) Date: Sep. 2, 2011

(87) PCT Pub. No.: WO2010/101226
PCT Pub. Date: Sep. 10, 2010

(30) Foreign Application Priority Data

Mar. 4, 2009 (JP) .................................. 2009-051312

(51) Int. Cl.
*C12N 15/88* (2006.01)
*C12N 15/11* (2006.01)

(52) U.S. Cl.
CPC .............. *C12N 15/88* (2013.01); *C12N 15/111* (2013.01); *C12N 2310/14* (2013.01); *C12N 2310/3515* (2013.01)

(58) Field of Classification Search
USPC .................. 435/6, 91.1, 91.31, 455, 458, 6.1; 514/44, 58; 536/23.1, 24.5, 22.1, 103; 424/450
See application file for complete search history.

(56) References Cited

U.S. PATENT DOCUMENTS

| | | | |
|---|---|---|---|
| 6,126,964 A | 10/2000 | Wolff et al. | |
| 6,265,387 B1 | 7/2001 | Wolff et al. | |
| 6,339,067 B1 | 1/2002 | Wolff et al. | |
| 7,166,745 B1 | 1/2007 | Chu et al. | |
| 7,173,154 B2 | 2/2007 | Chu et al. | |
| 2001/0009904 A1 | 7/2001 | Wolff et al. | |
| 2002/0001574 A1 | 1/2002 | Wolff et al. | |
| 2004/0063654 A1 | 4/2004 | Davis et al. | |
| 2005/0074769 A1* | 4/2005 | Fukuyama | 435/6 |
| 2005/0124069 A1 | 6/2005 | Chu et al. | |
| 2005/0164391 A1 | 7/2005 | Chu et al. | |
| 2005/0260597 A1 | 11/2005 | Chu et al. | |
| 2010/0048888 A1* | 2/2010 | Chen et al. | 540/108 |
| 2010/0063131 A1 | 3/2010 | Takeuchi et al. | |
| 2010/0167340 A1* | 7/2010 | Machida et al. | 435/68.1 |
| 2010/0190684 A1* | 7/2010 | Keay et al. | 514/2 |
| 2011/0224418 A1* | 9/2011 | MacLachlan et al. | 536/24.5 |
| 2012/0107229 A1* | 5/2012 | Huang et al. | 424/1.11 |
| 2012/0207734 A1* | 8/2012 | Jacky et al. | 424/94.3 |

FOREIGN PATENT DOCUMENTS

| | | |
|---|---|---|
| JP | 2002-529439 A | 9/2002 |
| JP | 2005-508394 A | 3/2005 |
| WO | 00/27795 A | 5/2000 |
| WO | 03/040375 A1 | 5/2003 |
| WO | 2006105361 | 10/2006 |
| WO | 2008117828 | 10/2008 |

OTHER PUBLICATIONS

Sayaka Toida, et al., "Cation-sei Cycloamylose for Gene Delivery", Polymer Preprints, Japan, 2008, pp. 4984-4985, vol. 57, No. 2.
BR 2005003479 A, (Universidade Federal De Minas Gerais), Mar. 13, 2007, 2 pages.
Guilherme D. Tavares, et al., "Development and physico-chemical characterization of cyclodextrin-DNA complexes loaded liposomes", Chem. Phys. Lett., 2006, pp. 507-512, vol. 429.
Murray S. Webb, et al., "The cationic lipid stearylamine reduces the permeability of the cationic drugs verapamil and prochlorperazine to lipid bilayers: implications for drug delivery", Biochimica Biophysica Acta., 1995, pp. 147-155, vol. 1238.
Mitsutaka Murata, et al., "Preparation and evaluation of liposome carrier for siRNA delivery containing novel additive", Summary of the 129th annual meeting of the Pharmaceutical Society of Japan, Mar. 5, 2009, p. 211, 26P-pm217.
Sayaka Toita, et al., "Cycloamylose-based Biomaterial: Nanogel of Cholesterol-bearing Cationic Cycloamylose for siRNA Delivery", Chemistry Letters, Oct. 31, 2009, pp. 1114-1115, vol. 38, No. 11.
Kentaro Kogure, et al. "Development of a non-viral multifunctional envelope-type nano device by a novel lipid film hydration method", Journal of Controlled Release, 2004, pp. 317-323, vol. 98.
Bartlett et al., "Impact of tumor-specific targetig on the biodistribution and efficacy of siRNA nanoparticles measured by multimodality in vivo Imaging", PNAS, 104(39):15549-15554 (2007).
Toita et al., "Functional Cycloamylose as a Polysaccharide-Based Biomaterial: Application in a Gene Delivery System", Biomacromolecules, 11(2):397-401 (2010).
Communication for EP 10748819.9, dated Feb. 12, 2014.
Communication for EP 10748819.9 dated Apr. 22, 2013, with Supplementary European Search Report.
Bartlett el al., "Physiochemical and Biological Characterization of Targeted, Nucleic Acid-Containing Nanoparticles", Bioconjugate Chem., 18:465-468 (2007).
Hu-Lieskovan et al., "Sequence-Specific Knockdown of EWS-FLI1 by targeted, nonviral delivery of small interfering RNA inhibits tumor growth in a murine model of metastatic Ewing's sarcoma", Cancer Res., 65(19):8984-8992 (2005).
Davis et al., "Self-assembling nucleic acid delivery vehicles via linear, water-soluble, cyclodextrin-containing polymers", Current Medicinal Chemistry, 11:179-197 (2004).

* cited by examiner

Primary Examiner — Jane Zara
(74) Attorney, Agent, or Firm — Sughrue Mion, PLLC

(57) ABSTRACT

This invention relates to a nucleic acid complex with low toxicity and high safety that can maintain a nucleic acid molecule capable of RNA interference or translation inhibition, such as siRNA or the like, in a cell; and a nucleic acid delivery composition that can efficiently deliver the nucleic acid complex into a cell. A nucleic acid complex with low toxicity and high safety that can maintain a nucleic acid in a cell can be obtained by forming a complex using a nucleic acid molecule capable of RNA interference or translation inhibition and a cycloamirose. Further, by using a carrier comprising (A) a diacylphosphatidylcholine, (B) cholesterol and/or a derivative thereof, and (C) an aliphatic primary amine as a nucleic acid delivery carrier to introduce the nucleic acid complex into a cell, the safety, efficiency of intracellular delivery, and persistence of the nucleic acid in the cell can be further improved.

15 Claims, 2 Drawing Sheets

NUCLEIC ACID COMPLEX AND NUCLEIC ACID-DELIVERING COMPOSITION

CROSS REFERENCE TO RELATED APPLICATIONS

This application is a National Stage of International Application No. PCT/JP2010/053581 filed Mar. 4, 2010, claiming priority based on Japanese Patent Application No. 2009-051312 filed Mar. 4, 2009, the contents of all of which are incorporated herein by reference in their entirety.

TECHNICAL FIELD

The present invention relates to a nucleic acid complex with low toxicity and high safety, which has an excellent ability to deliver a nucleic acid molecule capable of RNA interference or translation inhibition into a cell; and a nucleic acid delivery composition capable of efficiently delivering the nucleic acid complex into a cell.

BACKGROUND ART

Recent developments in biotechnology have led to the discovery of various nucleic acid molecules exhibiting intracellular RNA interference functions. For example, siRNA (small interfering RNA) is known by its ability to cause a degradation of the mRNA of a target gene in a cell, thereby inhibiting the expression of the target gene (RNA interference). This function of inhibiting the expression of the target gene due to RNA interference is effective for alleviating or treating disease presentations caused by abnormal expression of specific genes or gene clusters; therefore, the development of therapeutic agents using siRNA is expected. However, siRNA and other gene therapies pose a problem in that, because the nucleic acid molecule is a water-soluble, negatively charged polymer, it has an extremely low intracellular gene delivery efficiency, resulting in an inefficient therapeutic effect.

The use of a carrier (vector) is known to efficiently deliver genes into cells. Vectors are classified into viral and nonviral vectors. In spite of their high nucleic acid introduction efficiency, viral vectors have some safety concerns including pathogenicity, immunogenicity, and cytotoxicity. Therefore, the use of non-viral vectors is desired for clinical usage.

Examples of nonviral vectors include Lipofectamine™2000, which is already commercially available, a cationic lipid (see Patent Document 1) having a specific structure, and a composition (see Patent Document 2) containing an amphiphilic compound and polycation. Delivery of a nucleic acid molecule into a cell using a nonviral vector is performed by mixing a nucleic acid molecule with a nonviral vector to form a complex, and contacting the complex with the target cell. When the nonviral vector is capable of forming liposome, the vector is incorporated into a cell with a nucleic acid encapsulated in the liposome, thereby conducting intracellular nucleic acid delivery.

However, nucleic acid molecules capable of RNA interference, such as siRNA, have a particular characteristic; they are unstable and highly negatively charged. Therefore, the stability is problematically reduced when the nucleic acid molecule is mixed with a cationic vector as a nonviral vector due to charge neutralization, which hinders the continuous delivery of nucleic acid molecules into a cell. Although an example in which a nucleic acid is entrapped in a liposome by forming a complex of the siRNA and the cationic polymer is known (see Non-patent Document 1), its practical effectiveness has not been confirmed in terms of the cytotoxicity of the cationic polymer. Moreover, although known nonviral vectors can form stable complexes with nucleic acid molecules, the problem of insufficient delivery performance into a cell still remains, or, even when delivery is successful, the retention time of the complex in the cell is short. For these reasons, the known nonviral vectors have a defect in that they cannot maintain a nucleic acid molecule in the cell, hindering constant provision of the desired effects of the nucleic acid molecule.

In view of such prior art circumstances, there has been a demand for a technique that ensures high safety and low toxicity for delivering nucleic acid molecules, for example siRNA, capable of RNA interference or translation inhibition into a cell, and continuously maintaining the nucleic acid molecules therein.

PATENT DOCUMENT

[Patent Document 1] Japanese Unexamined Patent No. 2002-529439
[Patent Document 2] Japanese Unexamined Patent No. 2005-508394

NON-PATENT DOCUMENT

[Non-Patent Document 1] Kintaro Kogure et al., Development of a Non-viral multifunctional envelope-type nano device by a novel lipid film hydration method, J. Control. Release, 98 (2004) 317-323

SUMMARY OF INVENTION

Technical Problem

An object of the present invention is to solve the above problem of the prior art. Specifically, an object of the present invention is to provide a nucleic acid complex with low toxicity and high safety, which has an excellent ability to deliver a nucleic acid molecule capable of RNA interference or translation inhibition into a cell; and a nucleic acid delivery composition capable of efficiently delivering the nucleic acid complex into a cell. Another object of the present invention is to provide a medical composition containing the nucleic acid delivery composition and a method of delivering a nucleic acid molecule capable of RNA interference or translation inhibition into a cell by contacting the nucleic acid delivery composition with a cell.

Solution to Problem

The inventors of the present invention conducted extensive research to solve the above problems, and found that, by mixing a nucleic acid molecule (a nucleic acid molecule capable of RNA interference or translation inhibition) to be introduced into a cell and a cycloamylose compound, it becomes possible to form a complex that has low toxicity and high safety and is capable of delivering the nucleic acid molecule into the cell. The present inventors further found that the safety, effectiveness of intracellular delivery, and intracellular persistence of a nucleic acid can be further improved by using, as a nucleic acid delivery carrier for introducing the nucleic acid complex into the cell, a carrier comprising (A) a diacylphosphatidylcholine, (B) cholesterol and/or a derivative thereof, and (C) an aliphatic primary amine. The present invention was accomplished by conducting further research based on these findings.

Specifically, the present invention provides inventions with the following aspects:

Item 1: A nucleic acid complex comprising at least one cycloamylose compound selected from the group consisting of cycloamylose and derivatives thereof, and a nucleic acid molecule capable of RNA interference or translation inhibition.

Item 2: The nucleic acid complex according to Item 1, wherein the amount of the cycloamylose compound is 1 to 4,000 parts by weight per part by weight of the nucleic acid molecule capable of RNA interference or translation inhibition.

Item 3: The nucleic acid complex according to Item 1, wherein the cycloamylose compound has a polymerization degree of 10 to 500.

Item 4: The nucleic acid complex according to Item 1, wherein the nucleic acid molecule capable of RNA interference or translation inhibition is siRNA.

Item 5: The nucleic acid complex according to Item 1, which is an aggregate obtained by mixing a nucleic acid molecule capable of RNA interference or translation inhibition with a cycloamylose compound in an aqueous solution.

Item 6: A nucleic acid delivery composition comprising the nucleic acid complex according to any one of Items 1 to 5 and a nucleic acid delivery carrier.

Item 7: The nucleic acid delivery composition according to Item 6, wherein the nucleic acid delivery carrier is a composition comprising (A) a diacylphosphatidylcholine, (B) at least one member selected from cholesterol and derivatives thereof, and (C) an aliphatic primary amine.

Item 8: The nucleic acid delivery composition according to Item 7, wherein Component (A) in the nucleic acid delivery carrier is a diacylphosphatidylcholine in which the acyl moiety has 4 to 23 carbon atoms.

Item 9: The nucleic acid delivery composition according to Item 7, wherein Component (B) in the nucleic acid delivery carrier is cholesterol.

Item 10: The nucleic acid delivery composition according to Item 7, wherein Component (C) in the nucleic acid delivery carrier is an alkylamine having 10 to 20 carbon atoms.

Item 11: The nucleic acid delivery composition according to Item 7, wherein the molar ratio of Components (A):(B):(C) is 5-9:1-5:1.

Item 12: The nucleic acid delivery composition according to Item 7, wherein the nucleic acid delivery carrier is a liposome preparation in which a liposome membrane is formed from Components (A) to (C).

Item 13: A pharmaceutical composition comprising the nucleic acid delivery composition according to any one of Items 6 to 12.

Item 14: Use of at least one cycloamylose compound selected from the group consisting of cycloamylose and derivatives thereof, and a nucleic acid molecule capable of RNA interference or translation inhibition to produce a nucleic acid complex.

Item 15: Use of the nucleic acid complex according to any one of Items 1 to 5 and a nucleic acid delivery carrier to produce a nucleic acid delivery composition.

Item 16: Use of the nucleic acid complex according to any one of Items 1 to 5 to produce a medicament for delivering a nucleic acid molecule capable of RNA interference into a cell.

Item 17: A method for delivering a nucleic acid molecule capable of RNA interference into a cell, the method comprising the step of contacting at least one cycloamylose compound selected from the group consisting of cycloamylose and derivatives thereof, and a nucleic acid composition containing a nucleic acid molecule capable of RNA interference or translation inhibition, with a cell.

Item 18: The method according to Item 17 in which the nucleic acid delivery composition according to any one of Items 6 to 12 is contacted with a cell.

Advantageous Effects of Invention

The nucleic acid complex of the present invention, which is a nucleic acid complex obtained by forming a complex using a nucleic acid molecule capable of RNA interference or translation inhibition and a cycloamylose compound, is a highly safe nucleic acid complex that enables the nucleic acid molecule to be delivered into a cell and to be able to exert the RNA interference effect derived from the nucleic acid molecule in the cell. Further, the nucleic acid complex of the present invention can be readily combined with a nucleic acid delivery carrier, and can be easily encapsulated even in a nucleic acid delivery carrier in a liposome form. The complex of the present invention is therefore also excellent in its ease of formulation into a nucleic acid delivery composition. Furthermore, the nucleic acid delivery composition of the present invention can introduce the nucleic acid complex into a cell.

For delivering the nucleic acid complex of the present invention into a cell, the use of a carrier comprising (A) a diacylphosphatidylcholine, (B) cholesterol and/or a derivative thereof, and (C) an aliphatic primary amine, as a carrier for intracellular delivery can increase the efficiency of the intracellular delivery of the nucleic acid complex, and can further improve the persistence and safety of the intracellular delivery.

As explained above, the nucleic acid complex and the nucleic acid delivery composition of the present invention enables the nucleic acid molecule to effectively exert its RNA interference, and has high safety. Therefore, they are particularly useful as a medicament for gene therapy. Thus, the pharmaceutical composition or method of delivering a nucleic acid molecule capable of RNA interference or translation inhibition into a cell according to the present invention can deliver a nucleic acid molecule capable of RNA interference or translation inhibition into a cell more effectively.

BRIEF DESCRIPTION OF DRAWINGS

FIG. 1 shows the results of Test Example 2, more specifically the results of an evaluation of cell safety of the nucleic acid delivery composition (liposomalization and lipoplex method). In the figure, "control group" denotes a case in which the nucleic acid delivery composition of Example 2 was not added, "liposomalization" denotes a case in which the nucleic acid delivery composition of Example 2 prepared by liposomalization was added, and "lipoplex method" denotes a case in which the nucleic acid delivery composition of Example 2 prepared by the lipoplex method was added.

FIG. 2 shows the results of an evaluation of siRNA introduction into cells mediated by the nucleic acid delivery composition (liposomalization) in Test Example 3. The ordinate in FIG. 2 indicates the average fluorescence intensity per cell. In the figure, "liposomalization" denotes a nucleic acid delivery composition of Example 2 prepared by liposomalization.

DESCRIPTION OF EMBODIMENTS

Figure 1:
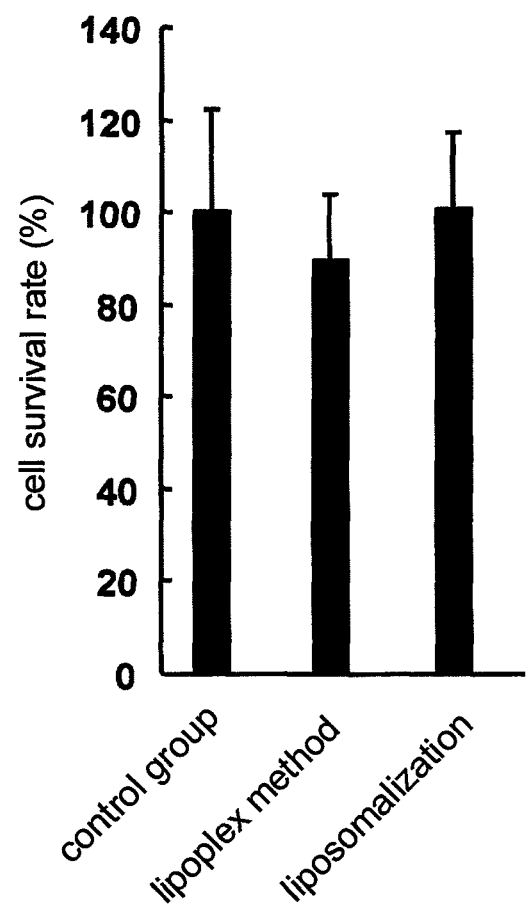
FIG. 1.

The present invention is more specifically explained below.
(1) Nucleic Acid Complex The nucleic acid complex of the present invention is characterized by comprising a nucleic acid molecule capable of RNA interference or translation inhibition, and a cycloamylose compound.

The type and the structure of the nucleic acid molecule used for the nucleic acid complex of the present invention are not particularly limited insofar as the complex is capable of RNA interference or translation inhibition inside a cell and exhibits its effect by being delivered into a cell. The number of bases of the nucleic acid molecule capable of RNA interference or translation inhibition is not limited insofar as an ability of RNA interference or an ability of inhibiting translation is ensured. For example, the molecule has 30 to 80 bases, preferably 38 to 64 bases, and more preferably 38 to 54 bases. In cases where the nucleic acid molecule forms a dimer or other multimeric complex, those exemplified base numbers of the nucleic acid molecule indicate the total base number of the dimer or other multimeric complex.

Examples of nucleic acid molecules capable of RNA interference or translation inhibition include any known molecules in the related field, such as RNA molecules, including siRNA, shRNA, miRNA, and antisense RNA. Among them, small RNA, such as siRNA, shRNA, and miRNA, and particularly siRNA, is preferable. siRNA has a drawback in that its stability decreases in the coexistence of known nonviral vectors; however, by being processed into the nucleic acid complex of the present invention, it is given a superior stability and an ability to be delivered into a cell. The base lengths of the sense strand and the antisense strand of siRNA are not particularly limited insofar as the strands ensure the siRNA interference ability; for example, the strands each have 10 to 50 bases, preferably 15 to 30 bases, more preferably 19 to 23 bases, and particularly preferably 21 bases. The siRNA may have a structure such that the sense strand and the antisense strand are hybridized and one or both of the two ends may form a protruding portion (dangling end) or a blunt end. Further, when one or both of the two ends in siRNA form a dangling portion, the dangling portion may be formed of a deoxyribonucleic acid (DNA).

Moreover, the target gene of the nucleic acid molecule capable of RNA interference or translation inhibition, in other words, the target gene subjected to suppression by RNA interference or translation inhibition is appropriately selected according to the intended use, etc., of the nucleic acid complex of the present invention. From a medical standpoint, it is known that, for example, the genes of transforming growth factor-$\beta$1 (TGF-$\beta$1), Smad3, monocyte chemoattractant protein-1 (MCP-1), platelet-derived growth factor (PDGF), connective tissue growth factor (CTGF), etc., are involved in specific diseases, and that suppression of the expression of these genes is effective to alleviate the diseases. Therefore, nucleic acid molecules capable of inducing RNA interference or translation inhibition of those genes are preferable example of the nucleic acid molecule.

The base sequence of the nucleic acid molecule capable of RNA interference may be designed according to the target gene. Any known base sequence designing methods in the related field may be used.

The nucleic acid molecule capable of RNA interference or translation inhibition used for the nucleic acid complex of the present invention may be derived from humans, animals, plants, bacteria, viruses or the like, or may be chemically synthesized. Further, the nucleic acid molecules may be single stranded, double-stranded or triple-stranded, and are not limited by molecular weight. Moreover, in the present invention, the nucleic acid molecule capable of RNA interference or translation inhibition may be modified chemically, enzymatically or by a peptide. Further, in the present invention, the nucleic acid molecules capable of RNA interference or translation inhibition can be used singly or in a combination of two or more.

The cycloamylose compound used for the nucleic acid complex of the present invention is at least one member selected from the group consisting of cycloamylose and derivatives thereof.

The cycloamylose is a cyclic $\alpha$-1,4-glucan formed of $\alpha$-1,4 bond of glucose, and has a stereoscopic hollow portion with a certain degree of depth inside the helix structure. The polymerization degree of the glucose in the cycloamylose used for the present invention is not particularly limited. For example, the polymerization degree is generally 10 to 500, preferably 10 to 100, and more preferably 22 to 50. The cycloamylose may be prepared from glucose using an enzyme, such as amylomaltase. Further, since cycloamylose is commercially available, the present invention may use a commercial product.

The cycloamylose derivatives used for the present invention are not limited insofar as they are pharmacologically acceptable. Examples thereof include derivatives containing alkyl, such as methyl, ethyl, propyl, or the like (carbon number=1 to 18); derivatives containing hydroxy alkyl, such as hydroxy methyl, hydroxy propyl, hydroxy propyl, or the like (carbon number=1 to 4); and derivatives containing sugar, such as monosaccharides, oligosaccharides, amino sugar, or the like.

In the present invention, cycloamylose or its derivative can be used singly or in a combination of two or more. Among cycloamylose and its derivatives, cycloamylose is preferable.

In the nucleic acid complex of the present invention, the ratio of the cycloamylose compound to the nucleic acid molecule is not particularly limited, but is usually 1 to 4,000 parts by weight, preferably 10 to 1,000 parts by weight, and more preferably 100 to 400 parts by weight, of the cycloamylose compound per part by weight of the nucleic acid. In terms of molar ratio, the above ratio is, for example, 0.1 to 1,000 mol, preferably 1 to 100 mol, and more preferably 10 to 20 mol, of the cycloamylose compound per mol of the nucleic acid. Satisfying such a ratio makes it possible to render more remarkable the continuity of intracellular delivery of nucleic acid by a nucleic acid delivery carrier, and the safety thereof.

The average particle diameter of the nucleic acid complex of the present invention is usually 6 to 60 nm, and preferably 8 to 40 nm. The average particle diameter of the nucleic acid complex is measured as a volume average particle diameter using a dynamic laser light scattering method.

The nucleic acid complex of the present invention is a complex formed by aggregation of the nucleic acid molecule and the cycloamylose compound. The nucleic acid complex of the present invention is produced by mixing the nucleic acid molecule and cycloamylose compound in a solution that can stably disperse the two substances. Specific examples of solutions that can stably disperse the nucleic acid molecule and cycloamylose compound include buffers such as Tris and the like. The buffers may contain chelating agents, such as ethylenediaminetetraacetic acid (EDTA), and the like. The conditions for mixing the nucleic acid molecule and the cycloamylose compound may be such that, in the above-mentioned solution, for example, about 0.1 $\mu$M to about 100 $\mu$M, preferably about 1 $\mu$M to about 10 $\mu$M, of the nucleic acid is mixed with about 1 $\mu$M to about 1,000 $\mu$M, and preferably about 10 μM to about 100 μM, of the cycloamylose compound, at room temperature for about 1 to 100 minutes, and preferably about 5 to 10 minutes. The thus produced nucleic acid complex of the present invention is present as a dispersion in the solution. The dispersion can be mixed as it is, or after dilution or concentration if necessary, with a nucleic acid delivery carrier.

(2) Nucleic Acid Delivery Composition

The nucleic acid complex is incorporated into a nucleic acid delivery carrier by being mixed with the nucleic acid delivery carrier, and thereby the nucleic acid molecule capable of RNA interference or translation inhibition is made deliverable into a cell. That is, the present invention also provides a nucleic acid delivery composition comprising the nucleic acid complex and a nucleic acid delivery carrier.

The nucleic acid delivery carrier is a non-viral vector used as a nucleic acid carrier to deliver (introduce) a nucleic acid molecule into a cell. The nucleic acid delivery composition is a composition used by being contacted with the cell into which the nucleic acid is to be delivered, in order to introduce the nucleic acid contained in the composition into the cell.

Formulation of Nucleic Acid Delivery Carrier

The nucleic acid delivery carrier used in the nucleic acid delivery composition of the present invention is not limited as long as it is capable of incorporating a nucleic acid complex into a cell. Examples of usable nucleic acid delivery carriers include known carriers, such as Lipofectamine™2000, and the like.

From the viewpoint of further improving the delivery performance of the nucleic acid molecule contained in the nucleic acid complex, and further improving the efficiency and safety of intracellular delivery, it is preferable to use, for example, a carrier comprising (A) a diacylphosphatidylcholine, (B) cholesterol and/or a derivative thereof, and (C) an aliphatic primary amine (hereinafter referred to as "Carrier 1").

The diacylphosphatidylcholine (hereinafter sometimes referred to as Component (A)) used in Carrier 1 is not limited as long as it is pharmacologically acceptable, and may be, for example, a diacylphosphatidylcholine in which the acyl moiety has 4 to 23 carbon atoms. The carbon numbers of the two acyl groups constituting the diacylphosphatidylcholine may be the same or different.

Specific examples of diacylphosphatidylcholines include dilauroylphosphatidylcholine, dimyristoylphosphatidylcholine, dipalmitoylphosphatidylcholine, distearoylphosphatidylcholine, dioleoylphosphatidylcholine, dilinoleoylphosphatidylcholine, myristoylpalmitoylphosphatidylcholine, myristoylstearoylphosphatidylcholine, palmitoylstearoylphosphatidylcholine, dibutyloylphosphatidylcholine, dihexanoylphosphatidylcholine, diheptanoylphosphatidylcholine, didecanoylphosphatidylcholine, diphthanoylphosphatidylcholine, didodecylphosphatidylcholine, dieicosanoylphosphatidylcholine, dihenicosanoylphosphatidylcholine, dierucoylphosphatidylcholine, diarachidonoylphosphatidylcholine, bis(tricosadinoyl)phosphatidylcholine, etc. Among these, preferable examples include diacylphosphatidylcholines in which the acyl moiety has 12 to 18 carbon atoms; more preferable examples include dimyristoylphosphatidylcholine, dipalmitoylphosphatidylcholine, distearoylphosphatidylcholine, myristoylpalmitoylphosphatidylcholine, myristoylstearoylphosphatidylcholine, palmitoylstearoylphosphatidylcholine, and like diacylphosphatidylcholines in which the acyl moiety has 13 to 17 carbon atoms; particularly preferable examples include dimyristoylphosphatidylcholine, dipalmitoylphosphatidylcholine, and distearoylphosphatidylcholine; and the most preferable examples include distearoylphosphatidylcholine. Such diacylphosphatidylcholines may be used singly or in a combination of two or more.

Cholesterol and/or a derivative thereof (hereinafter sometimes referred to as Component (B)) used in Carrier 1 is not limited as long as it is pharmacologically acceptable. Derivatives of cholesterol are cationic lipids with a cholesterol skeleton, and specific examples include 3β-[N—(N',N'-dimethylaminoethane)-carbamoyl]cholesterol (DC-Chol), 3β-[N',N',N'-trimethylaminoethane]cholesterol iodide (TC-Chol), bis(guanidinium)-tren-cholesterol (BGTC), N-cholesteryloxycarbonyl-3,7-diazanonan-1,9-diamine, β-alanine-diethanolamine-cholesterol, $N^4$-spermine cholesteryl carbamate (GL-67), N[$N^4$-3-aminopropylspermidine]cholesteryl carbamate (GL-78), $N^4$-spermine cholesteryl carboxamide (GL-90), N1,N8-bis(arginine carboxamide)-$N^4$-spermidine cholesteryl carbamate (GL-95), and N—[$N^1,N^4,N^8$-tris(3-aminopropyl)spermidine]cholesteryl carbamate (GL-96). Preferable examples of Component (B) include cholesterol. In Carrier 1, cholesterol and derivatives thereof can be used singly or in a combination of two or more as Component (B).

The aliphatic primary amine (hereinafter sometimes referred to as Component (C)) used in Carrier 1 is not limited as long as it is pharmacologically acceptable, and may be, for example, an alkylamine in which the alkyl moiety has 10 to 20 carbon atoms.

Specific examples of aliphatic primary amines include laurylamine, myristylamine, palmitylamine, stearylamine, oleylamine, decanoylamine, phthanoylamine, etc. Among these, alkylamines in which the alkyl moiety has 12 to 18 carbon atoms are preferable; stearylamine, oleylamine, and palmitoylamine are more preferable; and stearylamine is especially preferable. These aliphatic primary amines may be used singly or in a combination of two or more.

For Carrier 1 that comprises a combination of Components (A) to (C) described above, it is more preferable to have the following combinations in order to further improve the efficiency of intracellular delivery of a nucleic acid, and further reduce toxicity: (A) a diacylphosphatidylcholine in which the acyl moiety has 4 to 23 carbon atoms, (B) cholesterol and/or a derivative thereof, and (C) a $C_{10-20}$ alkylamine; and more preferably, (A) dimyristoylphosphatidylcholine, dipalmitoylphosphatidylcholine, and/or distearoylphosphatidylcholine, (B) cholesterol, and (C) stearylamine.

In Carrier 1, the ratio of Components (A) to (C) is not limited, and may be, for example, a Component (A):(B):(C) molar ratio of 5-9:1-5:1, preferably 6-9:1-4:1, and more preferably 7-8:2-3:1. Satisfying such a ratio makes it possible to achieve intracellular nucleic acid delivery with more improved efficiency and lower toxicity.

The total amount of Components (A) to (C) in the total amount of Carrier 1 is, for example, 1 to 100 wt %, preferably 20 to 90 wt %, and more preferably 30 to 70 wt %.

Carrier 1 may contain, in addition to Components (A) to (C), other cationic lipids. Specific examples of usable cationic lipids include squalamine, 3a,7a,12a-tris(3-aminopropoxy)-5β-cholan-24-(N,N-bis(3-aminopropyl)amine), 3a,7a,12a-tris(3-aminopropoxy)-5β-cholan-24-(N—(N-(3-aminopropyl))-3-aminopropyl)amine, 3a,7a,12a-tris(3-azidopropoxy)-5β-cholan-24-(N,N-bis(2-cyanoethyl)amine)), 3a,7a,12a-tris(3-azidopropoxy)-5,3-cholan-24-(N-(benzyloxycarbonyl)-N-(3-hydroxypropyl)amine), and like cationic lipids to which steroids are bound; umbrella-spermine conjugates and like cationic lipids to which cholic acid is bound; cationic lipids to which sterol glycoside is bound; cationic lipids to which steroid saponin is bound; dimethyldioctadecylammonium bromide salt (DDAB), 1,2-dimyristoyl-3-trimethylammonium propane, 1,2-dioleoyl-3-trimethylammonium propane (DOTAP), 1,2-dioleoyl-3-trimethylammonium propane methylsulfate, 1,2-dipalmitoyl-3-trimethylammonium propane, 1,2-distearoyl-3-trimethylammonium propane, N-(1-(2,3-bis(oleoyloxy) propyl)-N,N,N-trimethylammonium hydrochloride (DOTMA), dimyristoyloxypropyl dimethylhydroxyethylammonium bromide salt (DMRIE), dioleoyloxypropyl dimethylhydroxyethylammonium bromide (DORIE), dimethyldidodecylammonium bromide, N-(a-trimethylammonioacetyl)didodecyl-D-glutamine hydrochloride, N-(a-trimethylammonioacetyl)-O,O'-bis-(1H,1H,2H,2H-perfluorodecyl)-L-glutamine hydrochloride, O,O'-didodecanoyl-N-(a-trimethylammonioacetyl)diethanolamine hydrochloride, methylallyl didodecyl ammonium bromide, N-{p-(w-trimethylammoniobutyloxy)benzoyl}-didodecyl-L-glutamine hydrochloride, 9-(w-trimethylammoniobutyl)-3,6-bis(dodecanoyl)carbazole bromide, dimethyldioctadecyl ammonium hydrochloride, N-w-trimethylammoniodecanoyl-dihexadecyl-D-glutamine bromide, N-{p-(w-trimethylammoniohexyloxy)-benzoyl}-ditetradecyl-L-glutamine bromide, p-(w-trimethylammoniodecyloxy)-p'-octyloxyazobenzene bromide salt (MC-1-0810), p-{w-(b-hydroxyethyl)dimethyl-ammoniodecyloxy}-p'-octyloxyazobenzene bromide salt (MC-3-0810), O,O',O"-tridodecanoyl-N-(w-trimethylammoniodecanoyl)-tris(hydroxymethyl)aminomethane bromide salt (TC-1-12), 1,2-dilauryl-glycero-3-ethylphosphocholine, 1,2-dimyristoyl-glycero-3-ethylphosphocholine, 1,2-dipalmitoyl-glycero-3-ethylphosphocholine, 1,2-distearoyl-glycero-3-ethylphosphocholine, 1,2-dioleoyl-glycero-3-ethylphosphocholine, 1-palmitoyl-2-oreoyl-glycero-3-ethylphosphocholine, and like quaternary ammonium salt-type cationic lipids; etc.

When Carrier 1 contains a cationic lipid other than Components (A) to (C), the proportion of the cationic lipid is not limited as long as the effects of the present invention are not impaired, and may be, for example, 1 to 10 parts by weight, preferably 2 to 8 parts by weight, and more preferably 4 to 6 parts by weight, per 100 parts by weight of Components (A) to (C) in total.

Carrier 1 may further contain an oily base, if necessary. The addition of an oily base and the use of its properties enable the efficiency of nucleic acid introduction by Carrier 1 to be controlled. For example, when an oily base is added to adjust the specific gravity of Carrier 1, the contact of a cell with Carrier 1 can be controlled, thereby improving the introduction efficiency in vitro. Further, for example, when an oily base with a temperature sensitivity function is added, the core of the nucleic acid carrier can be disintegrated under predetermined temperature conditions to induce fluctuations in the cell surface, thereby improving the nucleic acid molecule introduction efficiency. Furthermore, for example, when an oily base that has an ability to be disrupted by an external stimulus is added, the core of Carrier 1 can be disintegrated by an external stimulus to induce fluctuations in the cell surface, thereby improving the nucleic acid molecule introduction efficiency.

Examples of oily bases that can be added to Carrier 1 include perfluorocarbon, perfluoropentane, perfluorooctyl bromide, perfluorohexane, perfluorotributylamine, soybean oil, refined soybean oil, hydrogenated soybean oil, unsaponified soybean oil, squalane, castor oil, clove oil, sorbitan trioleate, turpentine oil, safflower oil, safflower oil fatty acid, oleic acid, palm oil, rapeseed oil, fusel oil, olive oil, linseed oil, sesame oil, chlorophyll oil, croton oil, bergamot oil, cedar oil, orange oil, fennel oil, *eucalyptus* oil, corn oil, lavender oil, marjoram oil, lemon oil, cotton seed oil, coconut oil, egg yolk oil, rose oil, pine oil, almond oil, peanut oil, *camellia* oil, white camphor oil, chamomile oil, cinnamon oil, peppermint oil, esterified corn oil, ginger oil, Roman chamomile oil, snake oil, spearmint oil, sunflower oil, cacao butter, wheat germ oil, zinc oxide oil, hardened oils, hydrogenated vegetable oils, light liquid paraffin, liquid paraffin, medium chain fatty acid triglycerides, mink oil, bitter orange oil, polyoxyethylene castor oil, polyoxyethylene hydrogenated castor oil, polyoxyethylene hydrogenated castor oil 10, polyoxyethylene hydrogenated castor oil 100, polyoxyethylene hydrogenated castor oil 20, polyoxyethylene hydrogenated castor oil 40, polyoxyethylene hydrogenated castor oil 5, polyoxyethylene hydrogenated castor oil 50, polyoxyethylene hydrogenated castor oil 60, polyoxyl 35 castor oil, process oils, etc. Among such oily bases, perfluoropentane is temperature sensitive, and has the property of boiling at 29.5° C. and thereby becoming a gas. Further, perfluorohexane, perfluorooctyl bromide, and perfluorotributylamine have an ability to be disrupted by an external stimulus, and have the property of causing cavitation in the core of Carrier 1 and disintegrating it when receiving an external stimulus, such as ultrasonic irradiation.

When an oily base is contained, the proportion thereof is not limited as long as the effects of the present invention are not impaired, and may be, for example, 0.1 to 50 parts by weight, preferably 1 to 30 parts by weight, and more preferably 5 to 20 parts by weight, per 100 parts by weight of Components (A) to (C) in total.

Carrier 1 may further contain a membrane-fusogenic lipid (helper lipid) if necessary. When containing a membrane-fusogenic lipid, Carrier 1 has further improved intracellular nucleic acid molecule delivery efficiency. Examples of such membrane-fusible lipids include dioleoylphosphatidylethanolamine, dioleoylphosphatidylcholine, transphosphatidylphosphatidylethanolamine, 1,2-bis-(10,12-tricosadinoyl)-phosphoethanolamine, 1,2-dielaidoylphosphoethanolamine, 1,2-dihexadecylphosphoethanolamine, 1,2-dihexanoylphosphoethanolamine, 1,2-dilauroylphosphoethanolamine, 1,2-dilinoleoylphosphoethanolamine, 1,2-dimyristoylphosphoethanolamine, 1,2-dioleoylphosphoethanolamine, 1,2-dipalmitoleoylphosphoethanolamine, 1,2-dipalmitoylphosphoethanolamine, 1,2-diphytanoylphosphoethanolamine, 1,2-distearoylphosphoethanolamine, 1-palmitoyl-2-oleoylphosphoethanolamine, 1-palmitoyl-2-(10,12-tricosadinoyl)phosphoethanolamine, 1,2-dioleoylphosphoethanolamine-N-caproylamine, 1,2-dipalmitoylphosphoethanolamine-N-caproylamine, 1,2-dioleoylphosphoethanolamine-N,N-dimethyl, 1,2-dipalmitoylphosphoethanolamine-N,N-dimethyl, 1,2-dipalmitoylphosphoethanolamine-N-dodecanoyl, 1,2-dioleoylphosphoethanolamine-N-dodecanoyl, 1,2-dioleoylphosphoethanolamine-N-dodecanylamine, 1,2-dipalmitoylphosphoethanolamine-N-dodecanylamine, 1,2-dioleoylphosphoethanolamine-N-glutaryl, 1,2-dipalmitoylphosphoethanolamine-N-glutaryl, 1,2-dioleoylphosphoethanolamine-N-lactose, 1,2-dioleoylphosphoethanolamine-N-[4(p-maleimidemethyl) cyclohexane-carboxylate], dipalmitoylphosphoethanolamine-N-[4(p-maleimidemethyl)cyclohexane-carboxylate], 1,2-dipalmitoylphosphoethanolamine-N-[4(p-maleimidephenyl)butylamide], 1,2-dioleoylphosphoethanolamine-N-[4 (p-maleimidephenyl) butyrate], 1,2-dioleoylphosphoethanolamine-N-methyl, dipalmitoylphosphoethanolamine-N-methyl, 1,2-dioleoylphosphoethanolamine-N-[3-(2-pyridyldithio)propionate], 1,2-dipalmitoylphosphoethanolamine-N-[3-(2-pyridyldithio)propionate], 1,2-dioleoylphosphoethanolamine-N-(succinyl), 1,2-dipalmitoylphosphoethanolamine-N-(succinyl), etc. Among such lipids, dioleoylphosphatidylethanolamine can be advantageously used in Carrier 1.

When such a membrane-fusogenic lipid is contained, the proportion thereof is not limited as long as the effects of the present invention are not impaired, and may be, for example, 1 to 500 parts by weight, preferably 10 to 250 parts by weight, and more preferably 25 to 100 parts by weight, per 100 parts by weight of Components (A) to (C) in total.

Carrier 1 may contain various additives, such as isotonizing agents, excipients, diluents, thickeners, stabilizers, buffers, and preservatives; and/or aqueous vehicles, such as purified water, aqueous sugar solutions, buffer solutions, physiological saline, aqueous polymer solutions, and RNase free water, according to the utilization form. The amounts of such additives and aqueous vehicles to be added can be suitably selected according to the form of use of the nucleic acid delivery carrier.

Form of Nucleic Acid Delivery Carrier

The form of the nucleic acid delivery carrier is not limited insofar as the nucleic acid complex to be delivered into a cell can be encapsulated, but is preferably in the form of a liposome. For example, when Carrier 1 has the form of a liposome, Components (A) to (C), and optionally used other lipids, form a liposome membrane.

When the nucleic acid delivery carrier is in the form of a liposome, it may be a small unilamellar vesicle (SUV), a large unilamellar vesicle (LUV), or a multilamellar vesicle (MLV). The particle diameter thereof is suitably selected according to the type of cell into which the nucleic acid is delivered, and may be, for example, about 20 to 100 nm for SUV, about 200 to 1,000 nm for LUV, and about 400 to 3,500 nm for MLV. The particle diameter of the liposome is measured using a dynamic laser light scattering method.

Methods known in the art are used to produce the liposome and adjust the particle diameter thereof. For example, in the case of Carrier 1, a liposome may be formed by a thin film method, a reversed phase evaporation method, an ether injection method, a surfactant method, a heating method, or the like, using an oil phase containing Components (A) to (C) and an aqueous phase (aqueous vehicle). The particle diameter may be adjusted by an extrusion method, a French press method, a homogenization method, or the like.

Form, Formulation, and Method of Use of the Nucleic Acid Delivery Composition

When the nucleic acid delivery carrier is in the form of a liposome, the nucleic acid complex in the nucleic acid delivery composition of the present invention may be present in a state encapsulated within the inner aqueous phase of the liposome, or in a state bound to the inner or outer surface of the liposome membrane by an ionic or hydrophobic bond. The former state is preferable. Further, when the nucleic acid delivery carrier is in a form other than a liposome, the nucleic acid complex in the nucleic acid delivery composition of the present invention forms a lipoplex complex with components of the nucleic acid delivery carrier through an ionic or hydrophobic bond.

The nucleic acid delivery composition of the present invention is produced by mixing the nucleic acid complex with the nucleic acid delivery carrier and formulating the mixture into a desired form, or by mixing the ingredients of the nucleic acid complex and the nucleic acid delivery carrier composition in an arbitrary order and formulating the mixture into a desired form.

In the nucleic acid delivery composition of the present invention, the ratio of the nucleic acid complex to the nucleic acid delivery carrier depends on the type of nucleic acid complex, the type of nucleic acid delivery carrier, the type of target cell, etc. For example, the ratio may be 1 to 100 parts by weight, preferably 10 to 100 parts by weight, and more preferably 20 to 100 parts by weight, of the nucleic acid complex per 100 parts by weight of the total amount of the nucleic acid delivery carrier. More specifically, when Carrier 1 is used as the nucleic acid delivery carrier, the ratio may be 1 to 100 parts by weight, preferably 10 to 100 parts by weight, and more preferably 20 to 100 parts by weight, of the nucleic acid complex based on the total amount, i.e., 100 parts by weight of Components (A) to (C) contained in Carrier 1.

Further, in the nucleic acid delivery composition of the present invention, the content of the nucleic acid complex is not particularly limited; for example, the content of the nucleic acid complex in the nucleic acid delivery composition may be 1 to 50 wt %, preferably 10 to 50 wt %, more preferably 15 to 50 wt % based on the total content of the nucleic acid delivery composition.

Further, when Carrier 1 is used as the nucleic acid delivery carrier, the total amount of Components (A) to (C) contained in Carrier 1 may be, for example, 10 to 90 wt %, preferably 30 to 80 wt %, and more preferably 40 to 60 wt %, relative to the total amount of nucleic acid delivery composition.

The nucleic acid delivery composition of the present invention may contain various additives, such as isotonizing agents, excipients, diluents, thickeners, stabilizers, buffers, and preservatives; and/or carriers such as purified water, aqueous glucose solutions, buffer solutions, and physiological saline; according to the form of use. The amounts of such additives and carriers are selected according to the utilization form of the nucleic acid delivery composition.

The nucleic acid delivery composition of the present invention can be used by itself as a pharmaceutical for gene therapy, i.e., as a pharmaceutical composition for delivering a nucleic acid molecule capable of RNA interference or translation inhibition into a cell. When the nucleic acid delivery composition of the present invention is used as a pharmaceutical composition, the above-mentioned nucleic acid delivery carrier, additive, bases, are selected from those pharmacologically acceptable. When the nucleic acid delivery composition of the present invention is used as a pharmaceutical composition, the pharmaceutical composition may be formulated into various pharmaceutical forms. Examples of the form of the pharmaceutical composition of the present invention include liquid preparations, such as solutions (including syrups and the like), drops, and injections; and solid preparations, such as tablets, pills, powders, granules, and capsules (including soft capsules). When the pharmaceutical composition of the present invention is a liquid preparation, it can be preserved by freezing, or by freeze drying to remove water. Freeze-dried preparations, dry syrups, etc., are re-dissolved with water that has been distilled for injection use, water that has been sterilized, etc., at the time of use. Also, when the pharmaceutical composition of the present invention is a solid preparation, it can re-dissolved with water that has been distilled for injection use, water that has been sterilized, etc.

In the present invention, the cell into which the nucleic acid molecule capable of RNA interference or translation inhibition is to be delivered, or in other words, the target cell of the nucleic acid delivery composition of the present invention, is any cell insofar as it requires RNA interference or translation inhibition of the target gene by the nucleic acid molecule, or it is a cell inside a tissue that requires RNA interference or translation inhibition of the target gene. Examples thereof include a cultured cell, a cell isolated from an organism (including established cell lines), and a cell in vivo. They may be derived from a human or a non-human animal. The nucleic acid delivery composition of the present invention may be applied either in vitro, in vivo, or ex vivo.

Further, for example, if suppressing the expression of a specific gene in a tissue having a disease that is caused by the expression of said specific gene is effective for treating or alleviating the disease, the disease can be treated by introducing a nucleic acid molecule capable of RNA interference with respect to the specific gene into the cells of the diseased tissue.

In the present invention, a nucleic acid molecule capable of RNA interference or translation inhibition can be delivered into a cell through the step of contacting the nucleic acid delivery composition of the present invention with the cell. The method for contacting the nucleic acid delivery composition with a cell is not limited, insofar as a suitable amount of the nucleic acid delivery composition is contacted with the cell into which the nucleic acid molecule is to be introduced. For example, the method may be the same as a hitherto known method in gene therapy, and the same applies to the amount to be contacted: the method and amount are suitably selected. Therefore, application of the nucleic acid delivery composition of the present invention to a cell enables easy intracellular delivery of a nucleic acid molecule capable of RNA interference or translation inhibition, and maintains the delivered nucleic acid molecule stably in the cell.

For example, to contact the nucleic acid delivery composition of the present invention with a cell in vitro, the cell is cultured in the presence of a suitable amount of the nucleic acid delivery composition. Further, to contact the nucleic acid delivery composition of the present invention with a cultured cell or a cell isolated from an organism in vitro, the contact can be carried out in the presence of blood serum. To contact the nucleic acid delivery composition of the present invention with a cell in vivo, the nucleic acid delivery composition of the present invention may be contacted with the cell by, for example, direct injection into a tissue; intravenous, subcutaneous, intramuscular, interperitoneal, or intraocular injection, or injection into the digestive tract, a tooth, or the like; inhalation administration to the nasal cavity, oral cavity, lungs, or the like; oral administration; transdermal administration; transmucosal administration via the oral mucosa, vaginal mucosa, ocular mucosa, rectal mucosa, or uterine mucosa; or the like.

Further, when applying the nucleic acid delivery composition of the present invention to a cell, the application is performed with an effective amount of the nucleic acid delivery composition. For example, the amount of nucleic acid molecules capable of RNA interference or translation inhibition contained in the nucleic acid delivery composition is 0.001 pMol to 10 pMol, preferably 0.01 pMol to 1 pMol, and more preferably 0.01 pMol to 0.1 pMol, for each cell.

The nucleic acid delivery composition of the present invention enables intracellular delivery of a nucleic acid molecule capable of RNA interference or translation inhibition. More specifically, the nucleic acid delivery composition of the present invention is useful for delivering the nucleic acid molecule capable of RNA interference or translation inhibition, which has the form of a nucleic acid delivery complex and is contained in the nucleic acid delivery composition, into a cell by contacting the nucleic acid delivery composition with the cell.

(3) Method for Delivering a Nucleic Acid Molecule into a Cell

The present invention also provides a method for delivering a nucleic acid molecule into a cell. The method for delivering a nucleic acid molecule into a cell according to the present invention comprises the step of contacting the nucleic acid complex or nucleic acid delivery composition described above with the cell. The contact between the nucleic acid complex or nucleic acid delivery composition and the cell is not limited, insofar as a suitable amount of the nucleic acid complex or nucleic acid delivery composition is contacted with the cell into which a nucleic acid molecule is introduced.

By thus contacting the nucleic acid complex or nucleic acid delivery composition with a cell, the nucleic acid molecule can be stably maintained in the cell. For contacting with the cell, the nucleic acid complex may be used by itself or in combination with an additive or a carrier listed above. For more efficient intracellular nucleic acid molecule delivery, it is preferable to contact the nucleic acid delivery composition with the cell.

In the present invention, as mentioned above, the cell into which the nucleic acid molecule capable of RNA interference or translation inhibition is delivered is not limited insofar as it requires RNA interference or translation inhibition of the target gene by the nucleic acid molecule, or it is a cell inside a tissue that requires RNA interference or translation inhibition of the target gene. Examples thereof include a cultured cell, a cell isolated from an organism (including established cell lines), and a cell in vivo. They may be derived from a human or a non-human animal. The contact of the nucleic acid delivery composition of the present invention with the cell may be performed either in vitro, in vivo, or ex vivo.

Further, for example, if suppressing the expression of a specific gene in a tissue having a disease that is caused by the expression of said specific gene is effective for treating or alleviating the disease, the disease can be treated by introducing a nucleic acid molecule capable of RNA interference with respect to the specific gene into the cells of the diseased tissue.

For example, to contact the nucleic acid complex or nucleic acid delivery composition with a cell in vitro, the cell can be cultured in the presence of a suitable amount of the nucleic acid complex or nucleic acid delivery composition. To contact the nucleic acid complex or nucleic acid delivery composition with a cultured cell or a cell isolated from an organism in vitro, the contact can be carried out in the presence of blood serum. When contacting the nucleic acid complex or nucleic acid delivery composition with a cell in vivo, the nucleic acid complex or nucleic acid delivery composition may be contacted with the cell by, for example, direct injection into a tissue; intravenous, subcutaneous, intramuscular, interperitoneal, or intraocular injection, or injection into the digestive tract, a tooth, or the like; inhalation administration to the nasal cavity, oral cavity, lungs, or the like; oral administration; transdermal administration; transmucosal administration via the oral mucosa, vaginal mucosa, ocular mucosa, rectal mucosa, or uterine mucosa; or the like.

In the method for nucleic acid delivery into a cell according to the present invention, an effective amount of the nucleic acid complex or nucleic acid delivery composition is contacted with a cell to introduce the nucleic acid molecule capable of RNA interference or translation inhibition into the cell. For example, the amount of the nucleic acid complex or nucleic acid delivery composition to be administered is selected so that 0.001 to 10 pMol, preferably 0.01 to 1 pMol, and more preferably 0.01 to 0.1 pMol, of the nucleic acid molecules capable of RNA interference or translation inhibition are administered per cell.

The delivery method of the present invention may be performed by contacting the nucleic acid delivery composition with the cell.

EXAMPLES

The present invention is more specifically described below based on examples and the like; however, the present invention is not limited to these examples. In the following Examples and Test Examples, GL3-siRNA (siRNA to firefly luciferase; Dharmacon Research, Inc., (Boulder, Colo.), USA; sense: 5'-CUUACGCUGAGUACUUCGAdTdT (SEQ ID NO: 1), antisense: 5'-UCGAAGUACU-CAGCGUAAGdTdT (SEQ ID NO: 2) were used as siRNA. Cycloamylose (polymerization degree=22 to 50 (weight average molecular weight=6,000 to 8,000) Wako Pure Chemical Ind.) was used as cycloamylose.

Example 1

Preparation of a Complex Containing siRNA and Cycloamylose

A solution containing siRNA in a 2-µM concentration (siRNA solution) was prepared using a Tris-EDTA (TE) buffer solution (produced by Fluka Co., Ltd). Further, a solution containing cycloamylose in a 25-µM concentration (cycloamylose solution) was prepared using a Tris-EDTA (TE) buffer solution (produced by Fluka). Equal amounts of these solutions were mixed for one minute to form a siRNA complex.

Comparative Examples 1 to 4

Preparation of a Complex Containing siRNA and Cyclodextrin

A solution containing siRNA in a 2-µM concentration (siRNA solution) was prepared using a Tris-EDTA (TE) buffer solution (produced by Fluka Co., Ltd). Further, a solution containing α-cyclodextrin in a 2-µM concentration (α-cyclodextrin solution) was prepared using a Tris-EDTA (TE) buffer solution (produced by Fluka). Equal amounts of these solutions were mixed for one minute to form a siRNA complex (Comparative Example 1).

Under the same conditions as in Comparative Example 1 except for use of a solution containing siRNA in a 20-µM concentration (siRNA solution), a siRNA complex (Comparative Example 2) was prepared.

A solution containing siRNA in a 2-µM concentration (siRNA solution) was prepared using a Tris-EDTA (TE) buffer solution (produced by Fluka Co., Ltd). Further, a solution containing γ-cyclodextrin in a 2-µM concentration (γ-cyclodextrin solution) was prepared using a Tris-EDTA (TE) buffer solution (produced by Fluka). At room temperature, equal amounts of these solutions were mixed for one minute to form a siRNA complex (Comparative Example 3).

Under the same conditions as in Comparative Example 3 except for use of a solution containing siRNA in a 20-µM concentration (siRNA solution), a siRNA complex (Comparative Example 4) was prepared.

Test Example 1

Measurements of Particle Diameter and Zeta Potential of a siRNA Complex

The particle diameters of the siRNA complexes obtained in Example 1 and Comparative Examples 1 and 2, and the zeta potential of the solutions containing the siRNA complexes were measured. The particle diameters shown are the average particle diameters (nm) measured using a ZETASIZER 3000HSA (MALVERN INSTRUMENT) (the volume mean particle diameter was measured using a laser diffraction method). The zeta potential was measured using a ZETASIZER 3000HSA (MALVERN INSTRUMENT).

TABLE 1

|  | Particle Diameter (nm) | Zeta potential (mV) |
| --- | --- | --- |
| Example 1 | 33.0 | −12.8 |
| Comparative Example 1 | Not Detected | Not Detected |
| Comparative Example 2 | 400.0 | −25.2 |
| Comparative Example 3 | Not Detected | Not Detected |
| Comparative Example 4 | 631.4 | −32.0 |

Aggregation was observed in the siRNA complexes of Comparative Example 1-4

The results showed that, by producing a siRNA complex using cycloamylose, it is possible to produce a siRNA complex having a smaller particle diameter than those produced using α-cyclodextrin or γ-cyclodextrin. The smaller the particle diameter of the siRNA complex, the easier it is to be introduced into a cell. Therefore, it was confirmed that the siRNA complex using cycloamylose was suitable for intracellular delivery.

Example 2

Preparation of a Nucleic Acid Delivery Composition Containing a siRNA Complex

Distearoylphosphatidylcholine (DSPC), cholesterol, and stearylamine were weighed out in a molar ratio of 7:3:1, and dissolved in chloroform using an eggplant-type flask (recovery flask). The solution was dried under reduced pressure using a rotary evaporator to form a lipid thin membrane layer. The solution containing 0.014 mg/mL of a siRNA complex obtained in Example 1 was added to the resulting lipid thin membrane layer so that the solution had a DSPC concentration of 30 mg/mL, and then mixed. Thereafter, the particle diameter of the solution was adjusted by passing the solution through membranes having pore diameters of 800 nm and 200 nm using an extruder, to prepare a composition for siRNA delivery in a cationic liposome form (Example 2: liposomalization).

The Tris-EDTA (TE) buffer solution (produced by Fluka) was added to the resulting lipid thin membrane layer so that the solution had a DSPC concentration of 63.2 mg/mL, and then mixed. Thereafter, the particle diameter of the solution was adjusted by passing the solution through membranes having pore diameters of 800 nm and 200 nm using an extruder, to prepare a cationic liposome. Then, by mixing the resulting cationic liposome (DSPC concentration=63.2 mg/mL) and a solution containing a siRNA complex obtained in Example 1 (siRNA complex concentration=0.028 mg), a siRNA delivery composition was prepared (Example 2: lipoplex method).

Table 2 shows the properties of the obtained siRNA delivery composition (Example 2). The composition produced by adding a siRNA complex solution upon the formation of a cationic liposome (liposomalization) had a particle diameter of about 300 nm, and a zeta potential of 20 mV. As such, this composition was in a liposome form in which the particles had a uniform particle size. On the other hand, the composition produced by adding a siRNA complex solution after the formation of a cationic liposome (lipoplex method) had a particle diameter of about 800 nm, and a zeta potential of 20 mV. The particle diameter shown is an average particle diameter (nm) measured using a ZETASIZER 3000HSA (MALVERN INSTRUMENT) (the volume mean particle diameter was measured using a laser diffraction method). The zeta potential was measured using a ZETASIZER 3000HSA (MALVERN INSTRUMENT).

TABLE 2

| Preparation Method | Particle Diameter | Zeta Potential |
|---|---|---|
| Liposomalization | 319.5 | 24.9 ± 0.2 |
| Lipoplex Method | 869.6 | 19.2 ± 0.3 |

Nucleic acid delivery compositions were prepared using the siRNA complexes of Comparative Examples 1 or 3 under the same conditions as in Example 2. In these compositions, the siRNA complex also adhered to the surface of the liposome, showing that the siRNA complex was not sufficiently encapsulated in the liposome.

Test Example 2

Evaluation of the Inclusion Efficiency of siRNA

An FITC-labeled siRNA complex was prepared in the same manner as in Example 1 above, using FITC pre-labeled siRNA. Using the FITC-labeled siRNA complex, a nucleic acid delivery composition was prepared under the same conditions as in Example 2. The siRNA delivery composition immediately after preparation was precipitated by centrifugation (at 75,000 rpm for 1 hour), and the fluorescence intensity of FITC-labeled siRNA present in its supernatant was measured to calculate the siRNA inclusion efficiency (the proportion (%) of siRNA encapsulated in the liposome to the total siRNA).

As a result, as shown in FIG. 3, the inclusion efficiency of siRNA indicated high levels of 95.9% when prepared by liposomalization, and 91.5% when prepared by the lipoplex method. This revealed that the nucleic acid complex of the present invention had the feature of being efficiently introduced into a carrier for nucleic acid delivery in a liposome form. Although a restrictive interpretation is not desired, this is presumably because cycloamylose forms a compact complex with siRNA.

TABLE 3

| Preparation Method | Inclusion Efficiency (%) |
|---|---|
| Liposomalization | 95.9 |
| Lipoplex Method | 91.5 |

Test Example 3

Evaluation Test of Cellular Safety

An evaluation was conducted using an MTS assay. A CellTiter 96 Aqueous One Solution Cell Proliferation Assay produced by Promega Corporation was used for the MTS assay. Specifically, A594 cells (ATCC, USA) were inoculated at $3.16 \times 10^4$ cells per well into 200 μL of Dulbecco's Modification of Eagle's Medium (DMEM) containing 10 vol % of fetal bovine serum (FBS) in a 96-well plate, and incubated at 37° C. for 24 hours. After rinsing three times with Hank's Balanced Salt Solution (HBSS), the medium was changed to DMEM without FBS. The nucleic acid delivery composition of Example 2 (liposomalization and lipoplex method) was added in an amount of 20 μL per well and incubated at 37° C. under 5% $CO_2$ for 4 hours. Then, the culture supernatant in the wells was changed to DMEM with 10 vol % of FBS and again incubated at 37° C. under 5% $CO_2$ for 20 hours. Twenty μL of an MTS reagent and 100 μL of a DMEM medium with 10 vol % of FBS were added to each well, and incubated for two hours. The absorbance at 492 nm was determined, and cell viability was calculated. The cell viability was calculated by setting the absorbance at 492 nm, which was determined upon incubation under the above conditions without adding the nucleic acid delivery composition, to 100%.

FIG. 1 shows the results. As shown in FIG. 1, it became apparent that all nucleic acid delivery compositions prepared by liposomalization and the lipoplex method had low cytotoxicity and were highly safe. Particularly, it was confirmed that the nucleic acid delivery compositions of Example 2 prepared by liposomalization showed a significantly high level of safety.

Test Example 4

Evaluation Test of siRNA Delivery Efficiency into Cells

The intracellular introduction efficiency of siRNA was evaluated by measuring the fluorescence intensity of FITC-labeled siRNA using flow cytometry. In this test, a nucleic acid delivery composition prepared with FITC pre-labeled siRNA was used. Specifically, A594 cells (ATCC, USA) were inoculated at $5 \times 10^5$ cells/well into 500 μL of DMEM with 10 vol % of FBS in a 24-well plate, and incubated at 37° C. under 5% $CO_2$ for 24 hours. After rinsing three times with HBSS, 0.45 mL of DMEM containing no FBS was added. 0.05 mL of the nucleic acid delivery composition of Example 2 (Liposomalization: concentration of DSPC contained=30 mg/mL) was further added to each well, and the result was incubated at 37° C. under 5% $CO_2$ for 4 hours. Then, the culture supernatant in the wells was changed to DMEM with 10 vol % of FBS and incubated at 37° C. under 5% $CO_2$ for 20 hours again. Each well was rinsed with HBSS once, and 0.2 mL of CellScrubBuffer (produced by Gene Therapy Systems, Inc.) was added. Incubation was conducted at 37° C. under 5% $CO_2$ for 15 minutes. The wells were rinsed again with HBSS twice, and cells attached to the well bottom were detached using trypsin and collected by centrifugation. The resulting cells were suspended in HBSS. The suspension was filtered through a membrane having a pore diameter of 41 μm. The fluorescence intensity of the cells was measured using flow cytometry at 4 hours after the addition of the nucleic acid delivery compositions. As a control, the fluorescence intensity of the cells was measured in the same manner as described above, using a control nucleic acid delivery composition obtained by mixing a solution of Lipofectamine 2000™ (produced by Invitrogen Corporation), which is often used as a commercially available gene vector, diluted with OptiMEM media to 0.1 mg/mL, and a siRNA solution in which siRNA was diluted with TE buffer at a concentration of 2 μM in a volume ratio of 1:1.

Figure 2:
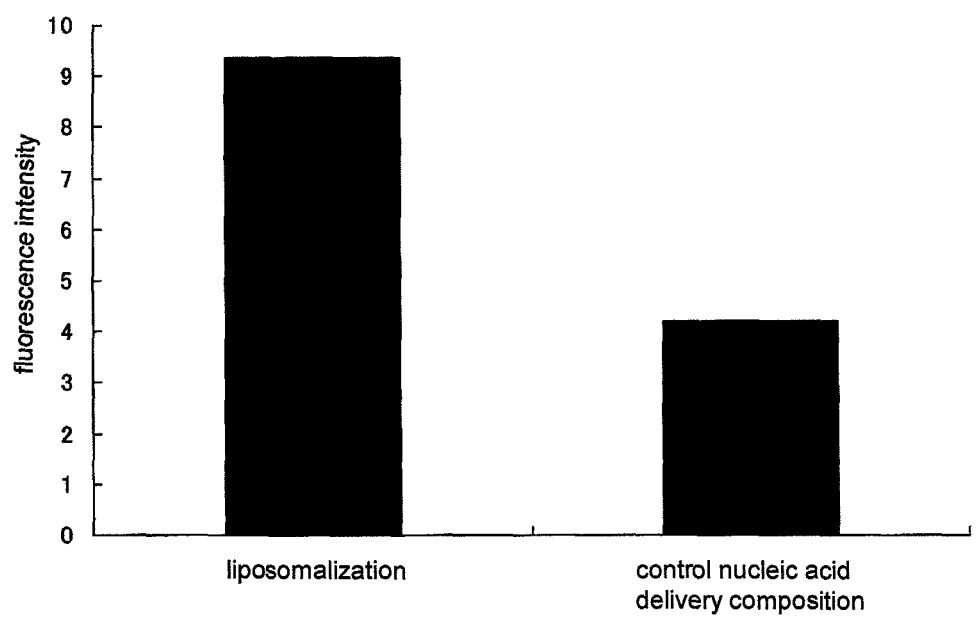
FIG. 2.

FIG. 2 shows the results. It was confirmed from the results that, for the nucleic acid delivery composition prepared in Example 2 (liposomalization), siRNA was significantly introduced into the cells.

The invention claimed is:

1. A nucleic acid complex comprising a cycloamylose and a nucleic acid molecule capable of RNA interference or translation inhibition, wherein the cycloamylose has a polymerization degree of 10 to 100.

2. The nucleic acid complex of claim 1, wherein the amount of the cycloamylose is 1 to 4,000 parts by weight per part by weight of the nucleic acid molecule capable of RNA interference or translation inhibition.

3. The nucleic acid complex of claim 1, wherein the nucleic acid molecule is a siRNA.

4. The nucleic acid complex of claim 1, in an aggregate form obtained by mixing the nucleic acid molecule with the cycloamylose in an aqueous solution.

5. A nucleic acid delivery composition comprising the nucleic acid complex of any one of claims 1-2 and 3-4 and a nucleic acid delivery carrier.

6. The nucleic acid delivery composition of claim 5, wherein the nucleic acid delivery carrier is a composition comprising (A) a diacylphosphatidylcholine, (B) at least one member selected from cholesterol and derivatives thereof, and (C) an aliphatic primary amine.

7. The nucleic acid delivery composition of claim 6, wherein (A) in the nucleic acid delivery carrier is a diacylphosphatidylcholine in which the acyl moiety has 4 to 23 carbon atoms.

8. The nucleic acid delivery composition of claim 6, wherein (B) in the nucleic acid delivery carrier is a cholesterol.

9. The nucleic acid delivery composition of claim 6, wherein (C) in the nucleic acid delivery carrier is an alkylamine having 10 to 20 carbon atoms.

10. The nucleic acid delivery composition of claim 6, wherein the molar ratio of (A):(B):(C) is 5-9:1-5:1.

11. The nucleic acid delivery composition of claim 6, wherein the nucleic acid delivery carrier is a liposome preparation in which a liposome membrane is formed from (A) to (C).

12. A pharmaceutical composition comprising the nucleic acid delivery composition of claim 5 and a pharmaceutically acceptable carrier.

13. A method for delivering a nucleic acid molecule capable of RNA interference into a cell, the method comprising:
    contacting a cycloamylose and a nucleic acid composition containing a nucleic acid molecule capable of RNA interference or translation inhibition, with a cell, wherein the cycloamylose has a polymerization degree of 10 to 100.

14. A method for delivering a nucleic acid molecule capable of RNA interference into a cell, the method comprising contacting the nucleic acid delivery composition of claim 6 with a cell.

15. The method of claim 14, wherein the molar ratio of (A):(B):(C) in the nucleic acid delivery composition is about 5-9:1-5:1.

* * * * *

```
                            SEQUENCE LISTING

<160> NUMBER OF SEQ ID NOS: 2

<210> SEQ ID NO 1
<211> LENGTH: 21
<212> TYPE: DNA
<213> ORGANISM: Artificial
<220> FEATURE:
<223> OTHER INFORMATION: Sense strand of GL3-siRNA
<220> FEATURE:
<221> NAME/KEY: modified_base
<222> LOCATION: (1)..(19)
<223> OTHER INFORMATION: RNA

<400> SEQUENCE: 1
cuuacgcuga guacuucgat t                                              21

<210> SEQ ID NO 2
<211> LENGTH: 21
<212> TYPE: DNA
<213> ORGANISM: Artificial
<220> FEATURE:
<223> OTHER INFORMATION: Antisense strand of GL3-siRNA
<220> FEATURE:
<221> NAME/KEY: modified_base
<222> LOCATION: (1)..(19)
<223> OTHER INFORMATION: RNA

<400> SEQUENCE: 2
ucgaaguacu cagcguaagt t                                              21
```